(12) United States Patent
Aslam

(10) Patent No.: US 11,116,648 B2
(45) Date of Patent: Sep. 14, 2021

(54) SYSTEM AND METHOD FOR CONTROLLING A PROSTHETIC DEVICE

(71) Applicant: United Arab Emirates University C/o Mohamed Al Hemairy m.hussien@uaeu.ac.ae; ip@uaeu.ac.ae, Al Ain (AE)

(72) Inventor: Zulfiqar M. Aslam, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 113 days.

(21) Appl. No.: 15/718,972

(22) Filed: Sep. 28, 2017

(65) Prior Publication Data
US 2019/0091041 A1    Mar. 28, 2019

(51) Int. Cl.
*A61F 2/70* (2006.01)
*A61F 2/68* (2006.01)
*A61F 2/50* (2006.01)
*A61F 2/76* (2006.01)

(52) U.S. Cl.
CPC ............ *A61F 2/68* (2013.01); *A61F 2/70* (2013.01); *A61F 2002/5036* (2013.01); *A61F 2002/5092* (2013.01); *A61F 2002/6827* (2013.01); *A61F 2002/6881* (2013.01); *A61F 2002/701* (2013.01); *A61F 2002/704* (2013.01); *A61F 2002/763* (2013.01); *A61F 2002/764* (2013.01); *A61F 2002/7615* (2013.01); *A61F 2002/7625* (2013.01); *A61F 2002/7685* (2013.01)

(58) Field of Classification Search
CPC .................. A61F 2002/7685; A61B 5/1125
See application file for complete search history.

(56) References Cited

U.S. PATENT DOCUMENTS

2003/0120183 A1\* 6/2003 Simmons .................. A61F 4/00
                                                                600/595
2006/0173552 A1\* 8/2006 Roy ........................ A61F 2/60
                                                                623/24

FOREIGN PATENT DOCUMENTS

TW          201206404 A1 \*  2/2012  ............... A61F 2/60

\* cited by examiner

*Primary Examiner* — David H Willse
(74) *Attorney, Agent, or Firm* — Hayes Soloway PC

(57) ABSTRACT

The present invention discloses a system and method for motion recognition and control of a prosthetic device. The system of the present invention uses a movement detector for detecting dimensional motion of a non-disabled physical appendage and generating motion information based on this detecting. The system further includes a microcontroller adapted to be connected to the movement detector for receiving and processing the motion information transmitted from the one or more movement detectors. The system controls a prosthetic device which has actuators that are configured to actuate motion of the prosthetic device based on the processing of the motion information.

20 Claims, 3 Drawing Sheets

SYSTEM AND METHOD FOR CONTROLLING A PROSTHETIC DEVICE

BACKGROUND

Field of Invention

The present invention relates to a system and method for controlling a prosthetic device, more particularly the present invention relates to a system and method for controlling a prosthetic device based on movement patterns perceived from a non-disabled appendage.

Description of Related Art

Prosthetic devices are currently widely used by disabled individuals and they are generally defined as apparatuses used as artificial substitutes for missing body parts, such as an arm, leg, hand or foot. A large number of individuals worldwide rely on prosthetic and/or orthotic devices to compensate for these disabilities, which include as amputation or debilitation, and to assist in the rehabilitation of injured limbs.

The number of disabled persons and amputees is increasing each year as the average age of individuals increases, as does the prevalence of debilitating diseases which affect limbs. As a result, the need for prosthetic and orthotic devices is also steadily increasing. Some conventional prostheses are equipped with basic controllers that artificially mobilize the joints without any interaction from the amputee and are capable of generating only basic motions. Such basic controllers do not take into consideration the dynamic conditions of the working environment or the exact desired motion by the user. The passive nature of these conventional prosthetics leads to movement instability, high energy expenditure on the part of the disabled person or amputee, gait deviations and other short- and long-term negative effects. This is especially true for arm and leg prostheses.

In recent years, the technology for orthotic and prosthetic devices has advanced to include basic sensor systems capable of providing some degree of feedback control, these sensors have mainly included proximity sensors, load sensors, accelerometers, tactile sensors, pressure sensors, and others. However, the sensors on these devices do not necessarily account for the user's desired movement as it relates to other functional limbs, and only take into account the movement of the prosthetic itself.

Other more advanced technologies have also been developed, which use electrical signals from muscle fibers, and transmit these signals to a controller in the prosthesis for actuating movements. These prostheses are commonly called myoelectric prosthetics. They operate by using electronic sensors to detect minute muscle, nerve, and EMG activity. The information from the sensors then translates this muscle activity (as triggered by the user) into information that its electric motors use to control the artificial limbs movements. Although this is a vast improvement from other types of prosthetics, including body powered prosthetics, it is often too expensive and unaffordable for the persons in need.

It is an objective of the present invention, to overcome the current drawbacks of available prosthetic devices, and provide a system and method of controlling a prosthetic device which is reliable, is not invasive, and is less costly than current designs.

It is a further objective of the present invention to provide a system and method of controlling a prosthetic device, which is capable of interacting with other physical appendages and other body parts of a user, with limited effort.

SUMMARY OF INVENTION

It is an object of the present invention to provide a system and method for the control of a prosthetic device. The system and method are designed so that a prosthetic device worn by a user can mimic corresponding movements made from a non-disabled corresponding appendage, such as a user's non-disabled arm, leg, foot, hand and so on.

It is to be understood that within this text, the use of the term "prosthetic device" or "prosthesis", is not intended to be limiting, and is defined to incorporate other types of devices or accessories which can be worn or controlled by a user, such as for example an orthotic device. An orthotic device can be defined as an external orthopedic appliance, that controls movement of specific body parts, e.g. knee braces, ankle foot braces, arm braces and so on.

In a first embodiment of the present invention, a system is disclosed for motion recognition and control of a prosthetic device. The system of this embodiment is comprised of:
 a movement detector for detecting dimensional motion of a non-disabled physical appendage and generating motion information based on said detecting;
 a microcontroller adapted to be connected to said movement detector for receiving and processing the motion information transmitted from the movement detector;
 a prosthetic device, adapted to be connected to the microcontroller, wherein the prosthetic device comprises one or more actuators which are configured to actuate motion of the prosthetic device based on said processing of the motion information.

According to an embodiment of the present invention, the prosthetic device is configured to mimic an identical motion performed by the non-disabled physical appendage of the user.

In accordance with one embodiment, the movement detector comprises one or more sensors, which comprise one or more motion sensors and one or more optical sensors. Preferably, the one or more motion sensors comprise depth sensors, such as a 9-axis sensor.

The depth sensors also preferably comprise an accelerometer, a gyroscope, a magnetometer and an e-compass, or a combination thereof.

In accordance with one embodiment, the processing motion information comprises mimicking a motion detected by the movement detector. This mimicked motion is conducted by the prosthetic device. Preferably, the mimicked motion is conducted in real-time by the actuators in the prosthetic device, as it is occurring in the non-disabled appendage. In one embodiment the one or more actuators comprise one or more motors.

In one embodiment, the one or more optical sensors include cameras, including RGB cameras, IR cameras, or monochrome cameras, or a combination thereof and an IR laser projector.

In one embodiment, the one or more motion sensors are located on or within the prosthetic device, or coupled and connected with the prosthetic device.

In one embodiment of the present invention, the prosthetic device is an electronic prosthetic device. The prosthetic device can comprise one or more actuators which enable the movement of the prosthetic device.

In accordance with one embodiment of the present invention, the prosthetic device is configured to mimic the motion detected from the non-disabled physical appendage in real-time. Thereby, the motions carried out by the non-disabled physical appendage can be mimicked by the prosthetic appendage as they occur.

In one embodiment, the microcontroller of the present invention is programmable using 4GL or 5GL code. This coding language is used to program the various motions to be carried out by the prosthetic device, as they are detected from the non-disabled appendage of the user in real-time.

In a further embodiment, the system of the present invention comprises memory component, wherein three dimensional positional data can be stored. The data can be obtained from the movement detector and stored for use in actuating movement in the prosthetic device at any time by the user. Therefore, in this embodiment, the prosthetic device does not need to actuate real-time movements as detected in the non-disabled appendage, but rather can actuate pre-stored movement commands, which have either been previously detected and stored from movements of non-disabled appendage, or have been independently programmed in the system.

In an additional embodiment of the present invention, the system further comprises a user interface adapted for programming movement patterns and for reading said movement patterns. The movement patterns are stored in the memory component, then processed by the microcontroller to send instructions to the actuators of the prosthetic device for the particular movement patterns to be carried out, once they are selected through the user interface.

In a further embodiment, the system comprises an authentication component which is comprised of authentication data associated with the user of the prosthetic device. The authentication component connected to the microcontroller comprising an input/output unit, a processor and a memory for storing the authentication data associated with the user of the prosthetic device. This authentication component can comprise biometric authentication means, wherein the biometric authentication means comprises a collection of data associated with characteristics of the non-disabled physical appendage.

In one embodiment, the authentication component input/output unit collects data associated with characteristics of the non-disabled physical appendage and stores the characteristics in the memory, and determines whether the dimensional motion detected by the motion detector originates from the non-disabled physical appendage before and as a condition of processing the motion information by the microcontroller.

In another embodiment, the microcontroller is preprogrammed with obstacle detection and avoidance capabilities. A movement pattern is performed by the prosthetic device based on the motion detected from the non-disabled physical appendage, or based on pre-stored movement patterns in the memory component. If the system detects an obstacle to the movement of the prosthetic device, then the actuators are instructed to terminate the movement, and/or alternatively take another path which may be stored in the memory. If no obstacle is detected then the movement pattern continues as instructed by the microcontroller to the actuators within the prosthetic device.

The present invention also discloses a method of controlling movements in a prosthetic device. The method of this embodiment comprises the following steps:

detecting a movement conducted by a non-disabled physical appendage;
transmitting said detected movement to a microcontroller;
processing motion information based on the transmitted detected movement; and
actuating motion of the prosthetic device based on the processed motion information.

In accordance with one embodiment of the present method, the motion actuated by the prosthetic device mimics an identical motion performed by the non-disabled physical appendage.

In accordance with an embodiment of the present method, the movement detector comprises motion sensors, which can comprise depth sensors, which have depth sensing capabilities, to detect the movement and positioning of the non-disabled physical appendage in three dimensions.

In one embodiment of the presently disclosed prosthetic control method, the prosthetic device is configured to mimic the motion detected from the non-disabled physical appendage in real-time. Thereby, the motions carried out by the non-disabled physical appendage can be mimicked by the prosthetic appendage as they occur.

In a further embodiment of the presently disclosed method, a 4GL or a 5GL code is used to program movement commands and positional data of the prosthetic device. This coding language is used to program the various motions, to be carried out by the prosthetic device, as they are detected from the non-disabled appendage of the user.

In a further embodiment, the method further comprises a step of detecting obstacles and carrying out obstacle avoidance commands. If an obstacle is detected the movement of the actuators is terminated, and/or an alternate movement path is instructed for the prosthetic device.

In one embodiment, the method further comprises an authentication step, prior to commencing motion commands. This incorporates authenticating data associated with the user of the prosthetic device, which comprises collecting and storing data associated with characteristics of the non-disabled physical appendage. This can include biometric data.

In a further embodiment, the present method incorporates the storing motion patterns conducted by the non-disabled appendage, for use in actuating movement in the prosthetic device at any time by the user. Therefore, in this embodiment, the prosthetic device does not need to actuate real-time movements as detected in the non-disabled appendage, but rather can actuate pre-stored movement commands, which have either been previously detected and stored from movements of non-disabled appendage, or have been independently programmed in the system.

BRIEF DESCRIPTION OF THE FIGURES

The accompanying figures are included to provide a further understanding of the invention, and are incorporated in and constitute a part of this specification. The figures illustrate embodiments of the invention and, together with the description, serve to explain the principles of the invention.

In the figures.

DETAILED DESCRIPTION

Figure 1:
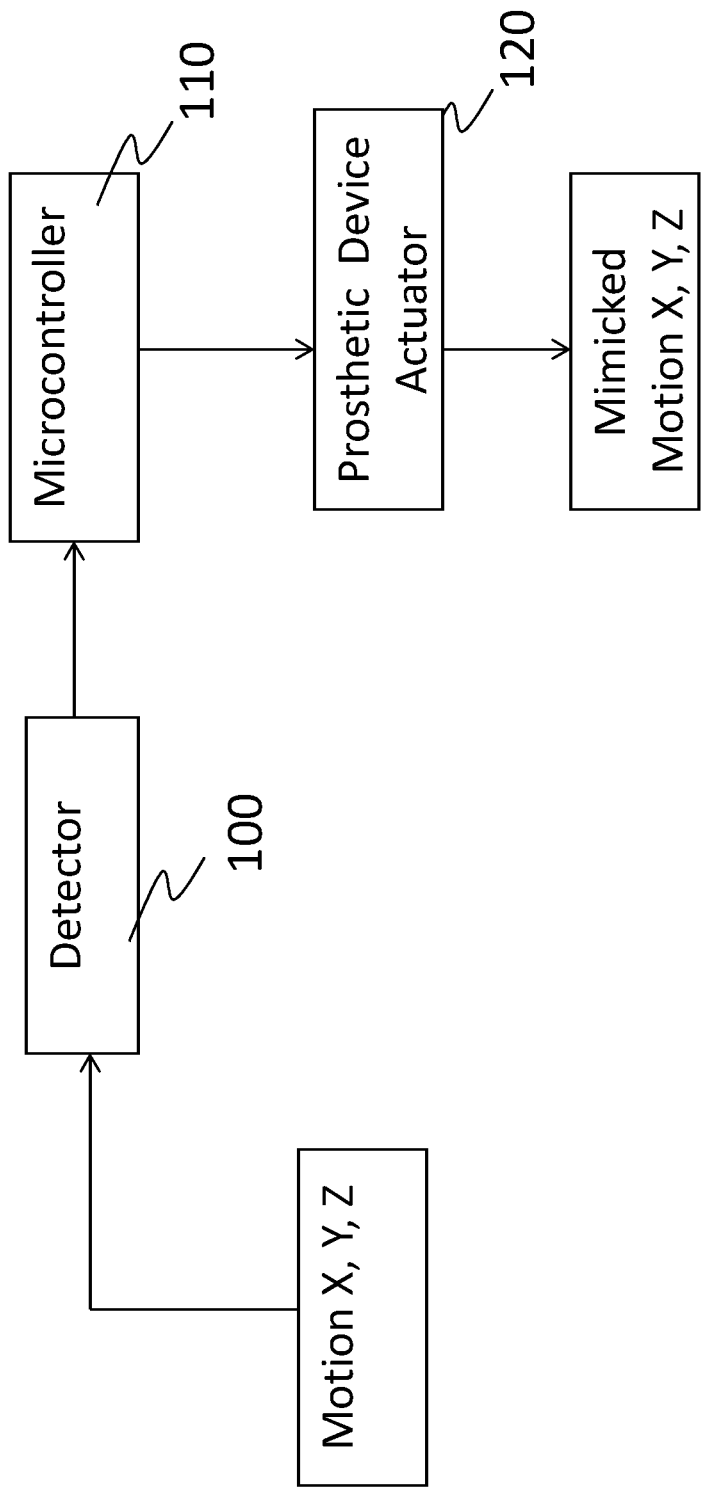
FIG. 1 illustrates a system in accordance with an embodiment of the present invention.

In the following Detailed Description, reference is made to the accompanying drawings, which form a part hereof, and in which is shown by way of illustration specific embodiments in which the invention may be practiced. Wherever possible, the same reference numbers are used in the drawings and the description to refer to the same or like parts. Directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Some preferred embodiments of the invention described herein relate generally to prosthetic and orthotic systems. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein The present invention pertains to a system and method for control of a prosthetic device. The advantages of the disclosed system and method will be made apparent through the detailed description, and include, the control of a prosthetic device, which incorporates a simplified system of components for sending movement, direction and positional information from a non-disabled appendage, and communicating this information to the prosthetic device, so that the same movement can be mimicked from the prosthetic device.

While the current advancements in this field include various control and sensing means for the operation of robotic/electronic prosthetic limbs, these are limited to the prosthetic device itself, and do not include components which can incorporate movements of another body part, such a user's corresponding arm, leg, hand, foot and so on. Hence it is an objective of the present invention to provide a system and method which allows a users healthy (non-disabled) appendage to aid in dictating the movements of a prosthetic appendage. This is particularly useful in the actuation of movements, where both corresponding body parts are required to move in unison, or in a specific motion pattern in order to completed a given motion specific task.

The advantages presented herein, include movement mimicking by a prosthetic device in real-time scenarios, or alternatively, pre-programmed and stored movements in a memory component of the system, which can be initiated by the user, without the need for mimicking movements from the non-disabled appendage. Further advantages will be made clear by the following description of exemplary embodiments.

Disclosed in the present invention is a system for motion recognition and control of a prosthetic device. The system comprises:
 a movement detector for detecting dimensional motion of a non-disabled physical appendage and generating motion information based on said detecting;
 a microcontroller adapted to be connected to said movement detector for receiving and processing the motion information transmitted from the one or more movement detectors;
 a prosthetic device, adapted to be connected to the microcontroller, wherein the prosthetic device comprises one or more actuators which are configured to actuate motion of the prosthetic device based on said processing of the motion information.

In one embodiment of the present invention, the prosthetic device is configured to mimic an identical motion performed by the non-disabled physical appendage.

For purposes of the examples and embodiments described herein, the non-disabled physical appendage can be a hand, an arm, a leg, a foot, a knee, fingers on a hand, joints throughout the body of a user, or other such appendages wherein a prosthetic device can be implemented and used. This list of appendages is merely exemplary and is not intended to limit the scope of the present invention in any way.

As can be seen in FIG. 1, and described in the above embodiment, a non-disabled physical appendage conducts a movement or specific set of motions in the x, y, and z directions (i.e. in three dimensions), and the system is configured so that this movement is detected by a movement detector 100. The data obtained from the movement detector 100 then transmitted to a microcontroller 110. This data is used by the microcontroller to send commands to the prosthetic device 120, which incorporates one or more actuators. The actuators are coupled to the prosthetic device 120 and carry out these commands and actuate an identical movement within the prosthetic device 120, as is being conducted by the non-disabled appendage.

In the present invention, we describe this movement by the prosthetic device as a mimicking movement, as this movement is directly aligned and closely identical to the movement conducted by the non-disabled appendage. Thusly, the motion which was conducted by the non-disabled physical appendage is then mimicked by the prosthetic device 120.

For example, if a user wishes to pick up a specific item with both arms/hands, the user would initiate a movement towards that item with their non-disabled appendage, and in real-time, the movement data is received from the sensors and cameras and the system can then actuate the same movement in the prosthetic device, which will result in the user being able to grasp the item with both hands in a similar fashion.

In one embodiment of the present invention, the movement detector 100 comprises one or more motion sensors. The motion sensors can comprise one or more depth sensors 200, and one or more optical sensors. Through the use of depth sensors 200, such as a 9-axis sensor, the detector is enabled to perceive multi-dimensional data as to the location, and movements of the non-disabled appendage. The three-dimensional data includes positioning data, and movements in the x, y, and z directions. This data can include information on various types of movements that are typically carried out by physical appendages, including but not limited to flexion, extension, adduction, abduction, rotation, and circumduction.

The movement detector 100 is coupled and connected to the prosthetic device 120 at a specific angle and position, so that it is capable to capture the three-dimensional positional and movement data derived from the non-disabled appendage. In one embodiment an additional back-up movement detector can be incorporated and attached to the individual and not the prosthetic device itself. In a preferred embodiment the movement detector 100 is embedded within or on the prosthetic device. The movement detector 100 of the present invention can detect and capture movement from gestures from angles up to 160 degrees. If it is desired to capture gestures falling outside this angle range then two or more units movement detectors can be incorporated with the prosthetic device.

In one embodiment, the movement detector 100 comprises one or more motion sensors which are located on or within, or coupled to the prosthetic device 120. Similarly the one or more optical sensors are located on or within, or coupled to the prosthetic device 120.

Figure 2:
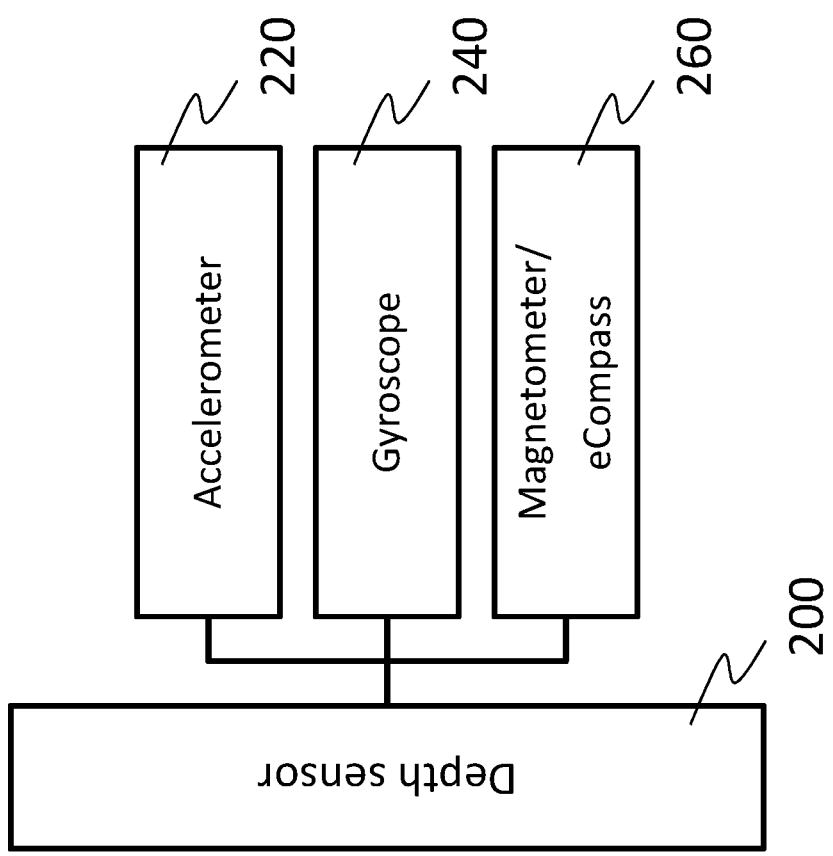
FIG. 2 illustrates an embodiment of the present invention.

As can be seen in FIG. 2, the one or more depth sensor 200, comprises at least one of an accelerometer, 220, a gyroscope 240, a magnetometer and or an e-compass 260. It further comprises one or more optical sensors.

In a preferred embodiment, the one or more optical sensors comprise one or more cameras, which can comprise RGB cameras, stereoscopic IR cameras, or monochrome cameras, or a combination thereof. The optical sensors further comprise an IR (infrared) imagining system, which is comprised of one or more IR cameras, and an IR laser projector. With the use of an IR laser projector, the one or more cameras can perform 3D scanning and depth perception of a non-disabled physical appendage as it is moving. The data/information generated and collected from these components can be used by a microcontroller 110 for actuating motion patterns by the prosthetic device actuator 120. Known sensors which comprise the above listed components and are used for depth imagining and movement capture can be incorporated into the current proposed system, such as for example Intel's RealSense infrared assisted 3D imagining system, which a person of skill in the art will already be familiar with.

The prosthetic device 120 operable in the currently disclosed system is preferably an electronic or robotic type prosthetic. That is the prosthetic is self-powered, and is not a body-type prosthetic which requires the user to physically move the prosthetic with their own body. The prosthetic device preferably comprises one or more actuators. These actuators allow the prosthetic device to carry out the movements which are detected from the non-disabled appendage, or pre-programmed or stored movement patterns of the prosthetic.

The actuators can comprise, for example one or more electrically controlled motors.

For the actuation of specific movements of the prosthetic device, the system incorporates software programs which can be coded using 4GL or 5GL code language. The programming of the system includes specific movement commands and motion pattern commands that can be actuated within the prosthetic device, depending either on the perceived movements of the non-disabled appendage, or prior pre-programmed and stored commands.

In one embodiment, the prosthetic device 120 is configured to mimic the motion detected from the non-disabled physical appendage in real-time, as the motion is occurring. In another embodiment, the prosthetic device control system can be configured to store three-dimension positional data and movement pattern commands in a memory component. The movement patterns can either be independently programmed patterns, or they can be movement patterns which were previously conducted by the non-disabled appendage and stored within memory of the system for actuating the same movement in the prosthetic device 120 at a later time.

For example, it can be envisioned that a movement pattern is first conducted in the real-time operation, wherein the prosthetic device 120 is mimicking the operations of the non-disabled appendage, such as a walking motion, from point A to point B. Once this movement has been conducted in real time, having a specific pace, direction, duration, and other such variables which are programmable, it can also be stored in the systems memory component as a movement pattern which can be repeated at a later time, without the necessity of the real-time monitoring of the movements of the non-disabled appendage. Therefore a user can have the option of conducting a specific movement pattern through already programmed movement patterns, without the necessity of using the motion sensors and cameras in real-time.

This can be extremely useful with simple repetitive tasks like walking from one room to another, or opening a door, or pushing wheels on a wheelchair, or other such repeatable actions which can be useful to a disabled person fitted with the prosthetic system of the present invention.

In one embodiment, the non-disabled physical appendage and the prosthetic device correspond to the same body part. For example, the appendage and the prosthetic device are arms. Alternatively, in another embodiment the non-disabled appendage and the prosthetic device do not correspond to same body part.

In accordance with further embodiment of the present invention, the disclosed system further comprises authentication components.

In a further embodiment, the system of the present invention further comprises an authentication component, which is comprised of authentication data associated with the user of the prosthetic device. The authentication component is connected to the microcontroller comprising an input/output unit, a processor and a memory for storing the authentication data associated with the user of the prosthetic device. The authentication component can be used to filter out perceived movements from the motion sensors and cameras, which are nearby in the range of detection, but do not correspond to the movements of the non-disabled appendage. This noise data picked up from the sensors or cameras can be properly authenticated and filtered out by the presently disclosed system, so as to optimize the operations of the prosthetic device and inhibit any undesired movements.

In one embodiment, the authentication component input/output unit collects data associated with characteristics of the non-disabled physical appendage and stores the characteristics in the memory, and determines whether the dimensional motion detected by the motion detector originates from the non-disabled physical appendage before and as a condition of processing the motion information by the microcontroller.

In one embodiment, the authentication component can comprise biometric authentication means. The biometric authentication means can be a collection of data associated with characteristics of the non-disabled appendage. Such as for example, hand shape, hand length, finger width and length, arm width and length, and a variety of combination of measurable biometric parameters.

The use of these authenticating biometric data or parameters would allow for the operations of the prosthetic device to be ceased, until the authentication process is conducted. The parameters can be stored in memory of the system, and used as identifying credentials for the operation of the prosthesis.

Also disclosed by the present invention is a method for controlling movements in a prosthetic device, to be used in accordance with the above described system. The method comprises the following steps:

detecting a movement conducted by a non-disabled physical appendage;

transmitting said detected movement to a microcontroller;

processing motion information based on the transmitted detected movement; and actuating motion of the prosthetic device based on the processed motion information.

Similarly, to the previously described system, the currently disclosed method motion allows for the prosthetic device to mimic an identical motion performed by the non-disabled physical appendage.

In one embodiment, the step of detecting a movement is conducted by a movement detector. In a preferred embodiment, the movement detector comprises one or more sensors, and preferably one or more depth sensors and optical sensors, wherein the optical sensors comprise one or more cameras.

The step of processing motion information comprises converting the motion information to movement command readable by one or more actuators.

The method further comprises steps wherein the prosthetic device mimics the motion detected from the physical appendage in real-time.

In another embodiment, the method further comprises storing motion patterns conducted by the non-disabled appendage, for use in actuating movement in the prosthetic device at any time by the user. This process was previously described above.

The method further comprises a step of using a user interface which is adapted to programming movement patterns and for reading said movement patterns. Therefore in one embodiment, the processing motion information comprises utilizing programmable movement patterns.

In accordance with a further embodiment, the method of controlling a prosthetic device further comprises an authentication step, which uses authenticating data associated with the user of the prosthetic device. The authentication step comprises use of biometric authentication means. This step can use biometric data collected and stored in the device, wherein the data is associated with characteristics of the non-disabled physical appendage. Examples of these characteristics were described above.

The method further includes authenticating the user by determining whether the detected movement originates from the user of the prosthetic device and actuating the motion of the prosthetic device only if it is the case.

In one embodiment the method further includes a step of authenticating the biometric data, prior to commencing motion commands of the prosthetic device.

Figure 3:
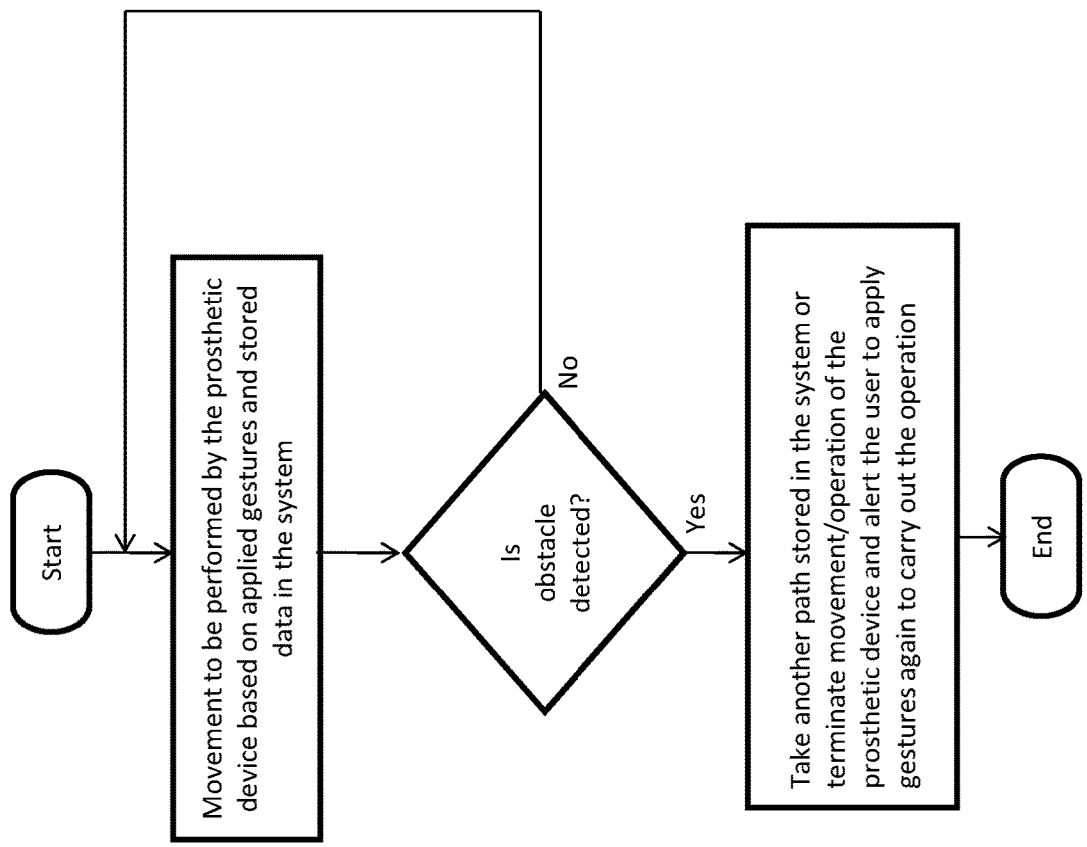
FIG. 3 illustrates an embodiment of the present invention.

As can be seen in FIG. 3, the present method further comprises steps for detecting obstacles and carrying out obstacle avoidance commands. For example, this process starts with a movement that is to be performed by the prosthetic device, based on the detected movement from the non-disabled appendage, and or pre-programmed movement patterns which are stored in the memory system of the prosthetic device. If an obstacle is detected, then the movement to be conducted by the prosthetic device is terminated and the user is alerted or another path is configured by the system. Alternatively, if an obstacle is not detected the movement by the prosthetic device carries on, as detected or as programmed.

For example, it can be envisioned that if a user who is equipped with a prosthetic device desires to go from location A to location B in his or her home repeatedly (provided that the location A is the identical location from which the user moved from last time) then the user can reactivate this movement path through a certain gesture for the same motion path already stored in the memory. If during this movement path, the user comes across an obstacle such as a person standing in the path or some other object placed in between, the depth sensor 200 which is already equipped with and communicates with a gyroscope, accelerometer and compass, capable of processing the complex motion fusion algorithms integrated with the one or more cameras, can terminate the movement of the actuators within the prosthetic device as soon as the obstacle is detected and alert the user to take another path configured by the system automatically or manually.

While selected embodiments have been selected to be illustrated of the present invention, and specific examples have been described herein, it will be obvious to those skilled in the art that various changes and modifications may be aimed to cover in the appended claims. It will, therefore, be understood by those skilled in the art that the particular embodiments of the invention presented here are by way of illustration only, and are not meant to be in any way restrictive; therefore, numerous changes and modifications may be made, and the full use of equivalents resorted to, without departing from the spirit or scope of the invention as outlined in the appended claims.

The invention claimed is:

1. A system for motion recognition and non-invasive control of a prosthetic device, the system comprising:
   a movement detector on the prosthetic device for detecting multi-dimensional motion of a non-disabled physical appendage and generating motion information based on said detecting;
   a microcontroller connected to said movement detector for receiving and processing the motion information transmitted from the movement detector;
   the prosthetic device, connected to the microcontroller, wherein the prosthetic device comprises one or more actuators which are configured to actuate motion of the prosthetic device, based on said processing of the motion information;
   wherein an authentication component collects data associated with characteristics of the non-disabled physical appendage and stores the characteristics in a memory, and determines whether the multi-dimensional motion detected by the movement detector matches characteristics of the non-disabled physical appendage collected and stored in the memory, as a condition of processing the motion information by the microcontroller.

2. The system of claim 1, wherein the movement detector comprises one or more sensors, wherein the one or more sensors comprise at least one motion sensor and at least one optical sensor.

3. The system of claim 2, wherein the one or more sensors comprise a depth sensor, wherein the depth sensor comprises at least one of, an accelerometer, a gyroscope, a magnetometer and an e-compass.

4. The system of claim 2, wherein the at least one optical sensor comprises one or more cameras, wherein the one or more cameras are RGB or monochrome cameras, or a combination thereof.

5. The system of claim 1, wherein processing the motion information comprises converting the motion information to movement commands readable by the one or more actuators.

6. The system of claim 1, wherein the processing motion information comprises mimicking a motion detected by the movement detector, wherein the motion is performed by the non-disabled physical appendage.

7. The system of claim 1, wherein the prosthetic device is configured to mimic the multi-dimensional motion detected from the non-disabled physical appendage in real-time.

8. The system of claim 1, further comprising a memory component, configured to store three dimensional positional data and movement patterns obtained from the movement detector.

9. The system of claim 8, wherein the microcontroller is preprogrammed with obstacle detection and avoidance capabilities, wherein if an obstacle is detected, movement instructed to the actuators is terminated, and/or an alternate path stored in the memory component is instructed by the microcontroller.

10. The system of claim 1, wherein the non-disabled physical appendage and the prosthetic device do not correspond to a same body part.

11. The system of claim 1, wherein the authentication component is connected to the microcontroller and comprises a processor and a memory for storing authentication data associated with a user of the prosthetic device.

12. The system of claim 1, wherein the authentication component is an input/output unit.

13. The system of claim 1, wherein the authentication component is a biometric authentication means.

14. A method for motion recognition and non-invasive movement control of a prosthetic device, the method comprising:
    detecting a movement conducted by a non-disabled physical appendage using a sensor on the prosthetic device;
    transmitting said detected movement to a microcontroller;
    processing motion information based on the transmitted detected movement and actuating motion of the prosthetic device based on the processed motion information;
    storing motion patterns conducted by the non-disabled appendage in a memory component for use in actuating movement in the prosthetic device at any time by a user of the prosthetic device; and
    authenticating the user by determining whether the detected movement matches the stored motion patterns of the non-disabled physical appendage and actuating motion of the prosthetic device only if it is the case.

15. The method of claim 14, wherein the step of detecting a movement is conducted by a movement detector, wherein the movement detector comprises one or more motion sensors and one or more optical sensors.

16. The method of claim 14, wherein processing the motion information comprises converting the motion information to movement commands readable by one or more actuators.

17. The method of claim 15, wherein the processing motion information comprises mimicking a motion detected by the movement detector, wherein mimicking the motion detected is actuated by the prosthetic device in real-time.

18. The method of claim 14, wherein the prosthetic device is configured to mimic an identical motion performed by the non-disabled physical appendage.

19. The method of claim 14, further comprising detecting obstacles and carrying out obstacle avoidance commands, wherein if an obstacle is detected the movement of actuators is terminated, and/or an alternate movement path is instructed by the microcontroller.

20. The method of claim 14, wherein authenticating the user further comprises authenticating biometric data of the non-disabled appendage.

* * * * *